United States Patent [19]

Hoyt et al.

[11] Patent Number: 4,586,080
[45] Date of Patent: Apr. 29, 1986

[54] METHOD AND APPARATUS FOR VIDEO INSPECTION OF ARTICLES OF MANUFACTURE

[75] Inventors: Mark Hoyt; Edward A. Rowe, both of Muncie, Ind.

[73] Assignee: Ball Corporation, Muncie, Ind.

[21] Appl. No.: 592,201

[22] Filed: Mar. 22, 1984

[51] Int. Cl.⁴ .............................................. H04N 7/18
[52] U.S. Cl. ..................................... 358/106; 358/101
[58] Field of Search ................ 358/106, 93, 101, 107; 455/602; 250/223 B

[56] References Cited

U.S. PATENT DOCUMENTS

| | | | |
|---|---|---|---|
| 2,798,605 | 7/1957 | Richards | 209/111 |
| 3,932,042 | 1/1976 | Faani et al. | 356/240 |
| 4,025,201 | 5/1977 | Deane | 358/106 |
| 4,380,025 | 4/1983 | Deane | 358/106 |
| 4,486,776 | 12/1984 | Yoshida | 358/106 |

FOREIGN PATENT DOCUMENTS 2260390  7/1974  Fed. Rep. of Germany ...... 455/602

*Primary Examiner*—Howard W. Britton
*Attorney, Agent, or Firm*—Gilbert E. Alberding

[57] ABSTRACT

Strobe lag is identified as a major source of sensitivity in distinguishing acceptable and flawed glassware in bright field video inspection systems employing strobed light sources and video systems with vidicon tubes. By disabling video signal generation from the photoconductive target of the vidicon for several milliseconds beginning with initiation of the strobed light sources, less sensitive and more stable operation of the video inspection apparatus is achieved. The video signal is generated from the fully developed stored image on the photoconductive target.

9 Claims, 2 Drawing Figures

METHOD AND APPARATUS FOR VIDEO INSPECTION OF ARTICLES OF MANUFACTURE

BACKGROUND OF THE INVENTION

This invention relates to a method and apparatus for inspecting articles of manufacture and, more particularly, relates to a method and apparatus for automatically inspecting such articles using video cameras and strobed momentary light beams.

Methods and apparatus for the inspection of articles of manufacture with video cameras is known. An example of such a method and apparatus are disclosed in U.S. Pat. No. 4,025,201. This patent discloses a method and apparatus in which the light is directed through an article on at least two different light paths to create two images that are directed upon a single, video camera. Preferably, decussate paths of light are generated with the article to be inspected placed at the intersection of the decussate light paths and with reflecting means to redirect the decussate light paths and their images onto the video camera at separate locations to permit the camera to view the images of each light path. Since both the images of the article can be scanned for defects, the entire area of the article or glass container may be scanned for defects during a single inspection period. The light beams may be generated by a single source used in connection with a reflective beam splitter to produce the decussate light paths, or two light sources may be used to produce the decussate beams. The preferable sources of light provide pulsed illumination which is substantially collimated.

U.S. Pat. No. 4,380,025 discloses another video inspection system for glass bottles in which the video signal of a video camera is electronically processed to determine defects in the bottles. This patent addresses the problem of rejecting satisfactory glassware articles because of images created by decorative bottle portions within the inspection region and the edges of the bottle, particularly at the shoulders of the bottle. In the system of U.S. Pat. No. 4,380,025, an artificial blanking unit is provided to inhibit inspection in variable blanking areas within the inspection region that can be positioned to correspond to the shoulders and decorated areas of the bottles. Inspection is inhibited within the blanking areas by artificial trigger pulses generated within the blanking area to generate an inhibit defect signal.

Another inspection apparatus is disclosed in U.S. Pat. No. 2,798,605. In U.S. Pat. No. 2,798,605, bottles are passed along a conveyor line and are passed in front of an optical system of a television camera. As each object passes in front of a camera, a light flash of short duration is provided to thereby illuminate the object and cause an image to be transmitted to the mosaic of a television camera tube. The mosaic is scanned by the cathode-ray gun of the camera tube which provides an output signal that indicates appreciable discontinuity in the video signal from its average level.

The above systems employ a video camera including a vidicon tube of a type known in the art. In the vidicon, the light image from the article being inspected is optically focused onto a photo-conductive target located at the face plate of the vidicon tube. At the target, this light produces an electrical-charge pattern corresponding to the various light intensities in the image on the target. By replenishing the charge deficiencies with electrons from a beam that scans the target, the light pattern is converted into a time sequence of current variations which is the video signal.

The scanning of the target is accomplished by swinging the electron beam across the target in a series of lines that are displaced vertically and in time into two interlaced individual rasters. The electron beam, in scanning the target, sweeps the target vertically at a rate of 60 hertz, while simultaneously sweeping it horizontally at the rate of 15,750 hertz.

The scanning electron beam is generated by the radiant heating of a cathode with a filament. The scanning beam is accelerated toward the photoconductive target with a fixed voltage of, for example, 350 volts, and is directed electrically within the vidicon in a trajectory that is nearly perpendicular to the target and is electromagnetically focused on the target.

During its unblanked scanning, the current variations in the electron beam are converted into voltage variations which are referenced to a compensated black level, are blanked during the intervals in which the scanning beam retraces horizontally and vertically across the target, are clipped at white and black peaks to obtain a usable signal between such extremes, are mixed with a signal to synchronize the scanning of the CRT of a television receiver, and are amplified to provide a composite video signal.

During the horizontal retrace at the end of each line and during the vertical retrace at the end of each raster field, the scanning electron beam is blanked, or turned off, to prevent the generation of unwanted noise to be added to the video signal. Normally, the electron beam is switched off with horizontal and vertical blanking pulses applied to the cathode of the image tube during the retrace intervals. The horizontal and vertical pulses and biasing potential used to turn off the scanning beam are developed by the normal camera circuits associated with a vidicon camera tube.

Video inspection systems of the type above, for example, described in the above-identified patents using strobed light sources to provide a bright field, have been, in the past, very sensitive in their ability to distinguish between the detection of such defects in glassware as birdswings, stuck glass, blisters, and the like. Such systems are difficult to adjust to reliably distinguish between satisfactory and flawed glassware.

SUMMARY OF THE INVENTION

It has now been discovered that this sensitivity problem is associated with "strobe lag" which is a photoconductive problem which results in a momentarily unusable signal from a vidicon tube after it receives a strobed light pulse. The cause of "strobe lag" is not understood; it may be due possibly to the delay in the stable and complete formation of the "electrical image in the photoconductive target layer, or to interference with such formation by the scanning electron beam as the image is developing on the photoconductive target surface. "Strobe lag" is differentiated from the lag due to persistence or incomplete erasure of a previous image due to insufficient beam current, which results in image smear or second or third field images in the analyzer. In the existing systems, described above, the image is projected onto the vidicon photoconductive target surface for a period of only about five microseconds during the strobe light pulse. "Strobe lag" appears from the strobe occurrence until approximately twelve milliseconds later when a peak usable signal is available. In the normal operation of a vidicon camera, sixteen milliseconds is available for each image element to form, sixteen milliseconds representing the interval between each raster occurring between vertical retraces. While "strobe lag" is not important in commercial television, it is important in the reliable image analysis needed in video inspection systems.

Photoconductive buildup time may be related to the capacitance between the transparent electrode, or target backplate, and the photoconductive layer of the target material. Most video amplifiers are very high impedance due to the low signal levels, typically 300 nanoamperes. The signals are capacitively coupled to the target and the RC time factors of the amplifiers and vidicon tube itself present an obstacle to simple solutions.

This invention provides a new and improved method and apparatus for optically inspecting articles of manufacture using a momentary beam of intense light to generate and direct an image of the article on the photoconductive target of a video camera. In accordance with the invention, the effects of "strobe lag" are reduced by interrupting the video signal from the photoconductive target during the generation of the momentary intense beam of light and resuming the video signal after a short duration to scan the stored image on the photoconductive target of the video camera. The video signal is preferably interrupted by blanking the scanning electron beam for at least twelve milliseconds and preferably for sixteen milliseconds to permit the "electrical image" to fully develop on the photoconductive target before effecting "normal" operation. Although the image may impinge on the photoconductive target of the vidicon for only a few microseconds, the storage time on the photoconductive target is on the order of one hundred milliseconds and a more reliable video signal can be developed from the stored electrical image.

By interrupting the generation of an image signal during the short duration normally associated with "strobe lag", it is possible to provide a bright field analyzer system with a more accurate and repeatable video output signal, to increase the vidicon tube life, to increase the reliability and performance in detecting birdswings, stuck glass, blisters, and other defects in round ware, and to increase the ability of the system to distinguish good and defective glassware.

The invention may be easily incorporated into existing video inspection systems for bright field analysis by using the existing video camera blanking means and adding to the system a means for generating a blanking signal of short duration following initiation of the momentary light beam and for energizing the vidicon blanking means for the time of the short duration. In its specific preferred embodiment, this added means can comprise a timing circuit actuated by a signal generated by the presence of an article to be inspected. The timing circuit generates a strobe trigger signal and a blanking signal of adjustable time duration from a simple resistance capacitance network and integrated circuit. The invention thus permits a substantial improvement in the operation of a video inspection system through a relatively simple and inexpensive apparatus modification.

BRIEF DESCRIPTION OF THE DRAWINGS

Other features and advantages of the invention will become more fully apparent from the drawings and description of the preferred embodiment in which.

DETAILED DESCRIPTION OF THE PREFERRED EMBODIMENT

Figure 1:
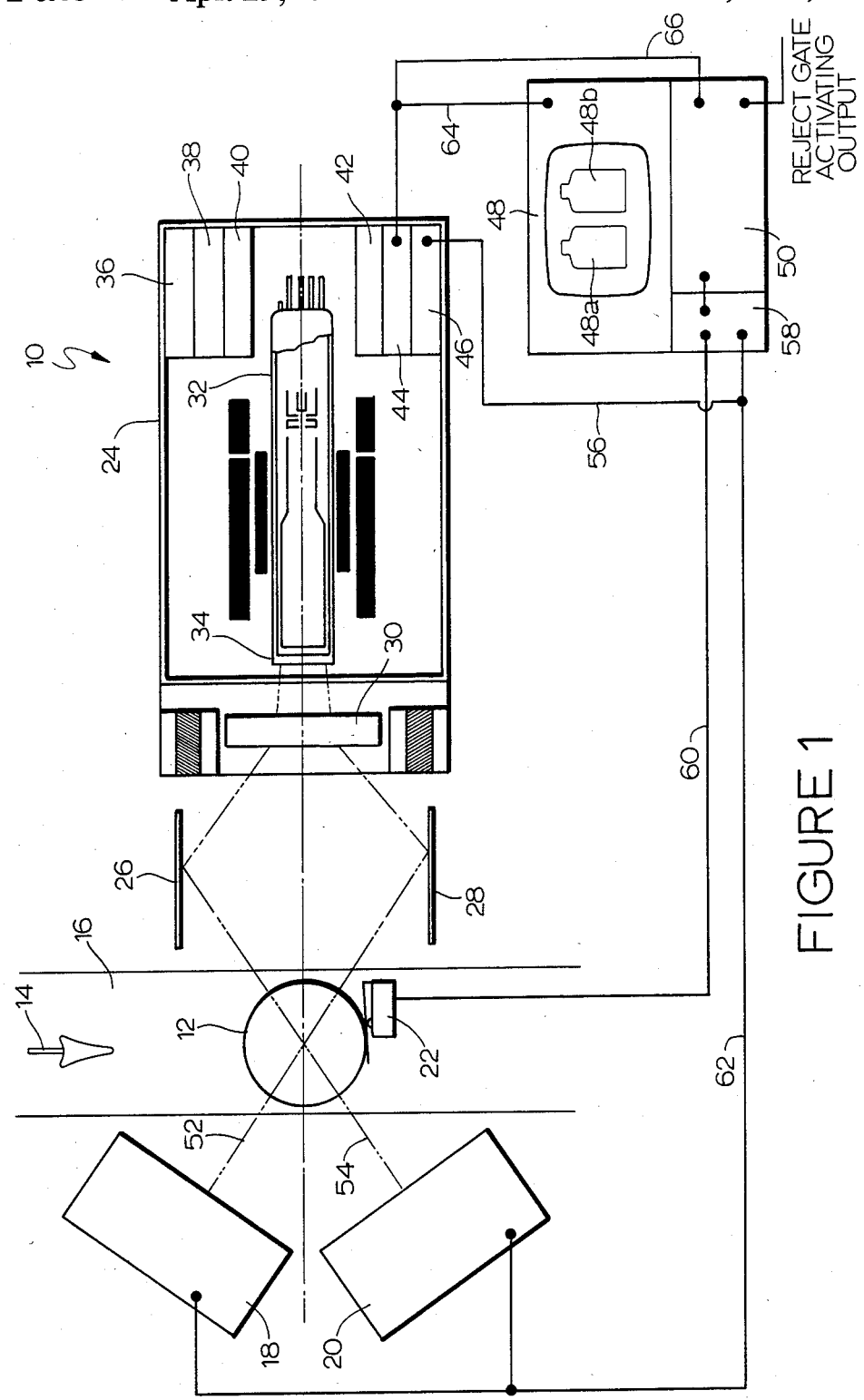
FIG. 1 is a diagrammatic view of an embodiment of a video-inspection apparatus practicing the invention.

In FIG. 1 articles 12, such as glass bottles, are carried past the video-inspection system 10 in the direction of arrow 14 by a conveyor 16. As each bottle passes the inspection station, it is inspected for defects or abnormalities, for example, spikes or birdswings. Detection of a defective bottle by the video-inspection system 10 can actuate a gate positioned downstream on the conveyor to direct the defective bottle off of the conveyor mechanism and into a reject container. In the normal operation, acceptable bottles are allowed to continue down the conveyor for further processing or packing while the reject bottles may be destroyed or the glass may be reused. The video-inspection station includes light sources 18 and 20 positioned on one side of and in close proximity to the conveyor. The light sources illuminate each of the glass bottle articles 12 as they pass thereby. The presence of a glass bottle at the inspection station may be detected by a microswitch 22 or by a separate photoelectric system or other such article-detecting means. Light sources 18, 20 may be semidefused light sources designed to illuminate the article under inspection in a manner known in the art. The light sources 18, 20 are preferably strobe lights providing a momentary beam of light, for example, having a duration of a few microseconds and preferably about five microseconds. The short intense beams from the strobe lights, in illuminating the relatively slowly moving article on the conveyor, provide images which are not blurred due to their movement.

In the system 10, a video camera 24 is positioned on the side of the conveyor 16 opposite the light sources 18, 20 and in alignment with image-directing means 26, 28, 30. The image-directing means may include any number of optical elements such as reflectors 26, 28 and reflecting and focusing means 30. The video camera 24 is of the type normally used to produce video images and employs a vidicon tube 32 to produce a video signal. The system directs the images of the article and focuses them on a photoconductive target 34 within the vidicon tube 32. In the operation of the camera, the photoconductive target 34 is scanned by an electron beam to produce electrical signals related to the image on the target. The video camera 24 includes circuit means 36 to provide the various voltages and currents needed to operate the video camera, circuit means 38 to provide a focused electron beam, circuit means 40 to provide horizontal scanning of the electron beam across the photoconductive target 34, circuit means 42 to provide vertical scanning of the electron beam across the photoconductive target 34, circuit means 44 to develop a video signal from the electron beam, and circuit means 46 to develop blanking signals for the electron beam. These circuit means are all standard video camera circuits and are well known in the art. The video camera circuit means 36, 38, 40, 42, 44, and 46 and the vidicon 32 are interconnected as well known in art to develop a video signal as generally described above.

If, for example, glassware being inspected has flaws, such as birdswings, blisters, changes in thickness, lettering, and so forth, the light passing through the glassware is deflected and the flawed portion appears darker in the image than in the satisfactory uniform regions. Accordingly, the image of the bottle projected onto the photoconductive target 34 of the vidicon tube 32 will include dark areas representing defects in the bottle. The photoconductive target will provide different electrical characteristics in regions that are exposed to different light intensities. The video signal generating means 44 of the video camera will produce an electrical signal carrying information about the electrical characteristics of the photoconductive target at the sites scanned, and this information is intended to reflect the condition of the article being inspected and to permit detection of flaws. The inspection station provides a TV monitor 48 and video signal analyzing means 50 to display and act upon the video signal and to identify signals representative of defects in the glassware being inspected. The monitor and video signal analyzing means are those in use in the art.

In the system shown in FIG. 1, the camera receives two images representing those generated in the two decussate paths of light. Thus, the video signal will represent light beams passing through the glassware article in two intersecting directions and permit the generation of signals generally representing the passage of light transversely through the entire periphery of the glassware.

FIG. 1 shows the system viewed from the top. The image-directing means 26, 28, 30 are located to bring the two decussate paths 52, 54 of light to the photoconductive target 34 of the video camera 24 in focus. The video camera 24 thus views the images engendered by light path 52 and the image engendered by light path 54 simultaneously. Both images are scanned for defects with the result that the glass article or glass container may be inspected from two generally orthogonal directions during a single inspection period. Preferably, the light paths 52, 54 intersect at a position corresponding to the central axis of the glassware article being inspected. Although FIG. 1 shows a system having decussate light beams, the invention may be used with a single light source.

As noted above, the video camera 24 shown in FIG. 1 is a standard commercial video camera employing a standard vidicon tube 32 of the type known in the art. The only modification to the video camera 24 is the introduction to the blanking circuit 46 of the video camera of a blanking signal over connection 56 from the means 58 introduced into the video inspection system to practice this invention.

The inspection station thus includes a television receiver 48, signal-analyzing circuitry 50, and means 58 for generating a signal having a timed short duration following initiation of the momentary light beam and for energizing said blanking circuit 46 of the video camera for the timed short duration.

In operation of the system, an article 12 is moved by conveyor 16 in the direction of the arrow 14. Upon arriving at the position indicated in FIG. 1, it trips the article-detecting means 22, which is shown as a microswitch, but may be any other means to detect the arrival of the article 12 at the position shown in FIG. 1. Such other means may include proximity sensors, photoelectric beams, and the like. Actuation of article-detecting means 22 provides a signal over connection 60 to the means 58 for generating a signal having a timed short duration and for energizing the blanking means 46. Upon sensing a signal on connection 60, the means 58 provides a signal over connection 62, tripping strobe lights 18, 20 which provide light beams 52, 54 for approximately five microseconds. The light beams 52, 54 create separate images of the article 12 which are directed by the means 26, 28, 30 onto the photoconductive target 34 of the vidicon 32.

In accordance with the invention, the vidicon tube 32 of camera 24 is prevented from generating a signal from photoconductive target 34 for a timed short duration that includes the illumination of the photoconductive target 34 by light sources 18, 20 and the imagedirecting system 26, 28, 30 and for a sufficient additional time for the photoconductive target 34 to fully develop a stable condition corresponding to the images of article 12. The duration in which the video signalgeneration means of video camera 24 is disabled is at least twelve milliseconds and preferably sixteen milliseconds, beginning upon triggering the light sources 18, 20. The video signal generation of video camera 24 is generally disabled by providing a blanking signal to the cathode of the vidicon tube 32 beginning with the triggering of light sources 18, 20 and continuing for more than at least twelve milliseconds thereafter. The means 58, therefore, generates, upon the arrival of an article 12 in position for inspection, a strobe trigger signal over connection 62 and a video blanking signal that continues for the timed short duration on connection 56 and is introduced into the blanking circuit 46 of video camera 24 to interrupt electron beam scanning the photoconductive target 34 for the timed short duration.

After this blanking period, the video camera means 44 will then develop an electrical signal (i.e., video signal) that is related to the images stored on the photoconductive target 34. This video signal is transmitted over video connections 64, 66 to the TV monitor 48 and signal-analyzing circuits 50, respectively. As indicated in FIG. 1, the TV monitor 48 generally displays the two images 48a, 48b of the article 12. The video signals over connection 66 are analyzed by the signal-analyzer 50 to differentiate between satisfactory articles and those which should be rejected.

Many circuits may be used as means for generating a signal having a timed short duration following initiation of the momentary beam of light and for energizing the video camera blanking circuits. The specific circuitry shown in FIG. 2 is preferred because it permits a simple and inexpensive means to introduce the invention into existing systems; however, with recognition of the invention, one skilled in the electronic arts may devise other circuitry to provide means 58.

Figure 2:
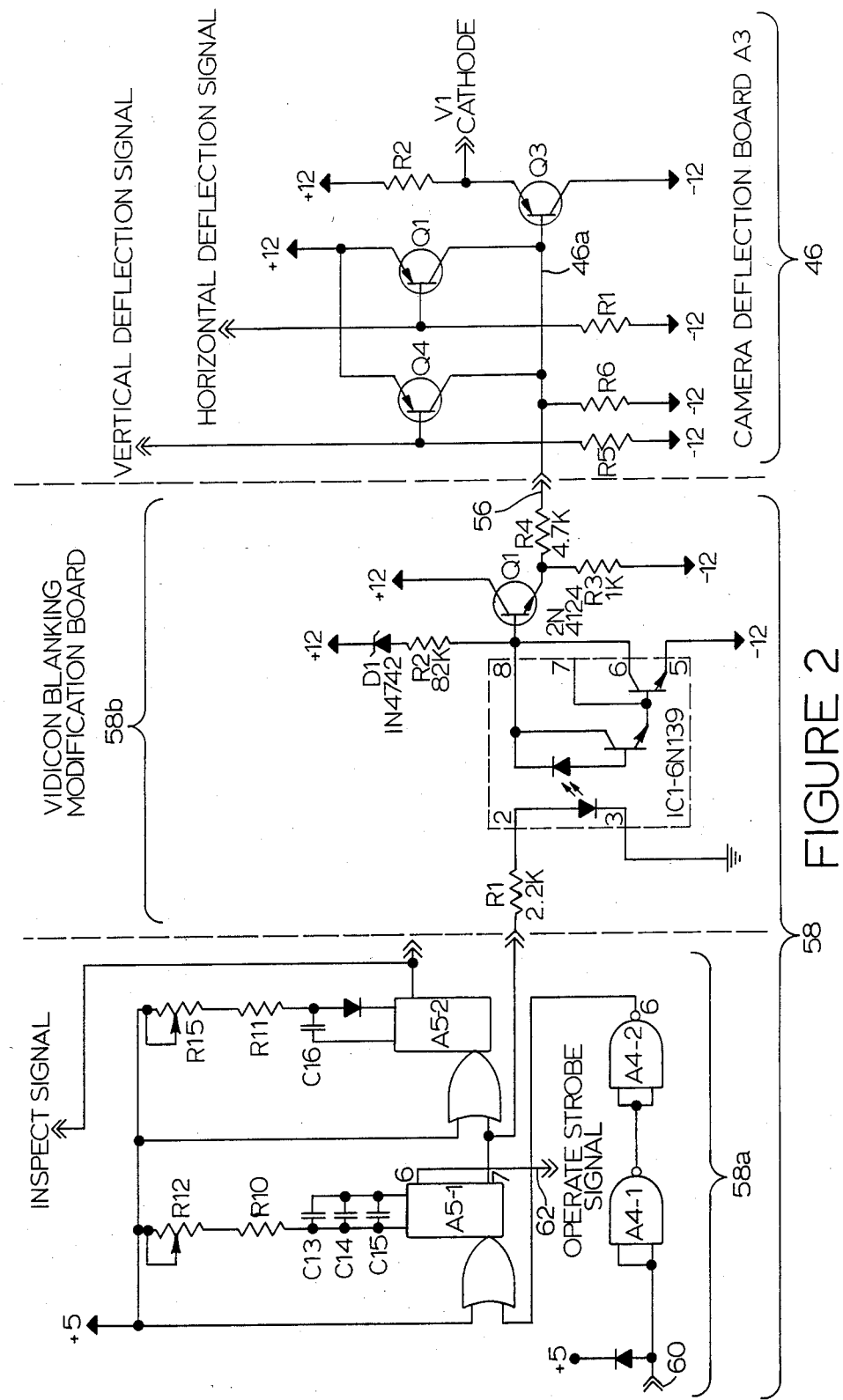
FIG. 2 is an electrical circuit diagram showing a preferred electrical circuit means in the system of FIG. 1 to practice the invention.

FIG. 2 thus shows a typical camera-deflection and blanking means 46 and a preferred means 58 for generating a signal having a timed short duration following the initiation of the momentary light beam and for energizing the video camera blanking means 46. Means 58 includes means 58a to generate a strobe-triggering signal, an inspection signal, and a blanking signal having a timed short duration determined by the resistance-capacitance network including R10, R12, C13, C14, and C15. Means 58 also includes an isolating and amplifying circuit 58b to electrically isolate the video camera circuitry from the circuitry of the remainder of the system.

In operation, a signal from the article detector 22 is presented at connection 60 at the input of a buffer A4. A4 pin 6 triggers the first half of flip-flop A5-1. A5-1 has two outputs: Q pin 6 and $\overline{Q}$ pin 7. Both output pulses at pins 6 and 7 are controlled by the resistance-capacitance time constant network consisting of R10, R12, C13, C14, and C15. The output at Q pin 6 provides a strobe-trigger signal over connection 62 as it goes high. Simultaneously, with the generation of the strobe-trigger signal at Q pin 6, $\overline{Q}$ pin 7 goes low; and this signal is supplied through resistor R1 to the input LED of IC1, turning off the LED in IC1. The signal from $\overline{Q}$ pin 7 also sets a A5-2 to be triggered. With the LED of IC1 off, the voltage outputs at pins 6 and 8 of IC1 change from about −11.4 volts to approximately −3 volts; and Q1, which acts like a switch, is turned on. The output of Q1 is coupled through resistor R4 over connection 56 to the video-blanking circuit 46 of the video camera where it is connected to line 46a which carries the horizontal and vertical retrace blanking signals of the video camera. In normal operation of the vidicon, the horizontal and retrace blanking signals swing from +11 volts to approximately −10 volts. When Q1 is turned on however, the line 46a can swing from +11 to only −5 volts. The −5 volts on the base of Q3 keeps Q3 biased off which keeps the electron beam turned off in the vidicon.

Thus, the generation of a low signal at $\overline{Q}$ pin 7 through the isolating and amplifying circuit 58b to line 46a of the camera-blanking circuit 46 will turn off the scanning beam of the vidicon for short time duration determined by the resistance capacitance network including R12, R10, C13, C14, and C15. Resistance R12 is adjusted to provide, preferably, a sixteen millisecond low-going pulse at $\overline{Q}$ pin 7 to blank the scanning beam of the vidicon during the sixteen milliseconds immediately following the generation of a strobe-triggering signal on line 60. At the end of this short duration (preferably sixteen milliseconds), $\overline{Q}$ pin 7 goes high triggering A5-2 to start the inspection timing period, and the signal analysis by signal-analyzing circuit 50 and simultaneously turns on the LED in IC1. IC1 output is turned on which turns off Q1 and allows the video-blanking circuit 46 to operate in a normal manner with blanking only during the normal horizontal and vertical retrace blanking periods.

The resistance capacitance network R10, R12, C13, C14, and C15 may be selected in any combination with the semiconductor circuit A5 to provide a timed pulse of at least twelve milliseconds duration and, preferably, at least sixteen milliseconds duration. Any multivibrator or adjustably timeable, pulse-generating circuitry can be used with any necessary buffers or amplifiers in producing the means 58. Means 58, as shown, includes a 6N139 opticisolator as IC1, a 2N4124 as transistor Q1, and a twelve-volt Zener diode IN4742.

Tests of the bright-field analyzer with the invention establish substantially improved performance and reliability and a substantial improvement in the range of sensitivity where good ware is passed and defective ware is rejected. Such tests include both static and dynamic tests. The static test is performed with the container stationary in the worst position for detection of flaws. The dynamic test is performed with containers passing through the system twenty-five times in eight positions. The control settings found to have the widest sensitivity range in the static test are used as a starting point in the dynamic tests. The dynamic tests are performed again after twenty-four hours to verify the test results and the real time operation of the system using the invention and selected ware.

In conducting the static tests, it was determined that incorporation of the invention increased the range of sensitivity by about seventy percent. In the dynamic tests, systems using the invention, showed an increase in the range of sensitivity of about sixty percent.

Although the preferred embodiment of the present invention has been shown and described, it should be understood that various changes and modifications in the preferred embodiment may be made by those skilled in the art without departing from the spirit and scope of the invention as defined in the following claims.

We claim:

1. In a method of optically inspecting an article including the steps of generating a momentary beam of light, directing the momentary beam of light at the article being inspected and further directing the beam of light and an image of the article onto a photoconductive target of a video camera, scanning the photoconductive target with an electron beam to produce a video signal representing the image of the article, and analyzing the video signal to determine flaws in the article, the improvement comprising:
   interrupting the video signal from the photoconductive target as generation of the light beam begins, and resuming video signal generation after a short duration to provide a video signal related to the stored image on the photoconductive target of the video camera.

2. In the method of claim 1, the steps of detecting the presence of an article in position for inspection, initiating a signal to generate the momentary beam of light and interrupting the generation of the video signal from the photoconductive target for at least twelve milliseconds.

3. In the method of claim 1 wherein the momentary beam of light is provided by a strobe light, the steps of generating a trigger signal for the strobe light and a blanking signal to interrupt the electron beam of the video camera for at least twelve milliseconds after the strobe trigger signal, triggering a strobe light to generate an intense light beam of several microseconds duration, and allowing the electron beam to resume scanning the stored image on the photoconductive target after at least twelve milliseconds.

4. The method of claim 3 wherein the object is glassware and the method includes the steps of generating two decussate light beams with the article at their intersection and wherein the decussate light beams are directed to create an image on the photoconductive screen by each light beam.

5. Apparatus for optically inspecting an article with a momentary beam of light, comprising:
   a video camera,
   a source of a momentary beam of light,
   means for directing the momentary beam of light at the article to be inspected and for directing the light beam and an image of the article onto the video camera,
   said video camera including a photoconductive target upon which the image of the object is focused, means for scanning the photoconductive target with an electron beam, means for blanking the electron beam of the scanning means, and means for developing from the electron beam a video signal corresponding to the image during unblanked scanning periods, and
   means for generating a signal upon the initiation of the momentary beam of light and continuing for a timed short duration thereafter and for operating said blanking means for said timed short duration.

6. The apparatus of claim 5 wherein operation of the apparatus is commenced by means creating a signal from the presence of the article to be inspected, the source of the momentary light beam is a strobe light, and the means for generating a signal of short duration is a semiconductor circuit providing said strobe light trigger signal and the blanking signal having a timed short duration.

7. The apparatus of claim 6 wherein the semiconductor circuit has means having a normal state and a triggered state connected with the blanking means of the video camera, said triggered state providing a signal to the blanking means to interrupt the electron beam for about sixteen milliseconds and said normal state providing no operation of the blanking means.

8. The apparatus of claim 6 wherein the means for generating a signal of short duration includes a printed circuit board having an opticisolator having input connected with the means generating the blanking signal of short time duration and an output connected with a semiconductor switch whose output controls the blanking means of the video camera.

9. The apparatus of claim 5 wherein the source of momentary light beam is a strobe light, the means for generating a blanking signal having a timed short duration comprises a timing circuit actuated by the presence of an article to be inspected and generating a strobe light trigger signal and an blanking signal of adjustable time duration, said adjustable time duration being developed by a resistance-capacitance network in the timing circuit.

* * * * *